United States Patent [19]
Solar

[11] Patent Number: 5,474,537
[45] Date of Patent: Dec. 12, 1995

[54] INFLATABLE SHAFT CATHETER

[75] Inventor: Ronald J. Solar, San Diego, Calif.

[73] Assignee: Pameda N.V., Curacao, Netherlands

[21] Appl. No.: 402,776

[22] Filed: Mar. 9, 1995

Related U.S. Application Data

[63] Continuation of Ser. No. 214,041, Mar. 16, 1994, abandoned, which is a continuation of Ser. No. 859,219, Mar. 30, 1992, abandoned.

[51] Int. Cl.$^6$ ................................................. A61M 25/00
[52] U.S. Cl. ................................................. 604/96; 604/192
[58] Field of Search ............ 604/96–103; 606/192–196; 600/18

[56] References Cited

U.S. PATENT DOCUMENTS

| | | | |
|---|---|---|---|
| 3,044,468 | 7/1962 | Birtwell | 604/99 X |
| 3,053,257 | 9/1962 | Birtwell | 604/97 |
| 3,906,938 | 9/1975 | Fleischhacker . | |
| 3,973,556 | 8/1976 | Fleischhacker . | |
| 4,349,033 | 9/1982 | Eden | 128/660 |
| 4,406,656 | 9/1983 | Hattler et al. . | |
| 4,467,790 | 8/1984 | Schiff | 604/96 X |
| 4,538,622 | 9/1985 | Samson et al. . | |
| 4,545,390 | 10/1985 | Leary . | |
| 4,554,929 | 11/1985 | Samson . | |
| 4,601,713 | 7/1986 | Fuqua . | |
| 4,619,274 | 10/1986 | Morrison . | |
| 4,719,924 | 1/1988 | Crittenden et al. . | |
| 4,734,093 | 3/1988 | Bonello et al. | 604/95 |
| 4,757,827 | 7/1988 | Buchbinder et al. . | |
| 4,762,129 | 8/1988 | Bonzel . | |
| 4,793,350 | 12/1988 | Mar et al. | 604/96 X |
| 4,813,434 | 3/1989 | Buchbinder et al. . | |
| 4,815,478 | 3/1989 | Buchbinder et al. . | |
| 4,820,349 | 4/1989 | Saab . | |
| 4,892,519 | 1/1990 | Songer et al. | 604/96 |
| 4,927,413 | 5/1990 | Hess | 604/95 |
| 4,944,740 | 7/1990 | Buchbinder et al. . | |
| 4,958,634 | 9/1990 | Jang | 606/194 |
| 4,976,689 | 12/1990 | Buchbinder et al. . | |
| 5,040,548 | 8/1991 | Yock . | |
| 5,041,089 | 8/1991 | Mueller et al. | 604/96 |
| 5,106,368 | 4/1992 | Uldall et al. | 604/43 |
| 5,143,093 | 9/1992 | Sahota | 128/898 |
| 5,160,321 | 11/1992 | Sahota | 604/96 |

FOREIGN PATENT DOCUMENTS

| | | |
|---|---|---|
| 0304258 | 2/1989 | European Pat. Off. . |
| 0462801 | 12/1991 | European Pat. Off. . |
| 0462482 | 12/1991 | European Pat. Off. . |

Primary Examiner—John D. Yasko
Assistant Examiner—Adam J. Cermak
Attorney, Agent, or Firm—Cowan, Liebowitz & Latman

[57] ABSTRACT

The invention herein is directed to a dilatation catheter comprising a steering wire, a dilatation balloon encompassing the said steering wire, and a flexible, inflatable catheter shaft concentric to the steering wire and in fluid communication with the balloon.

15 Claims, 4 Drawing Sheets

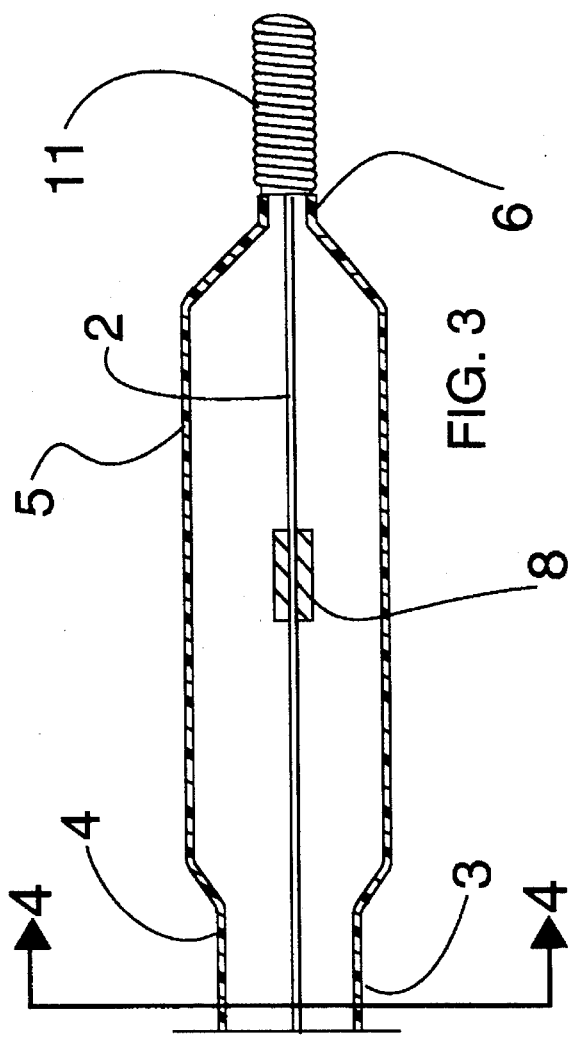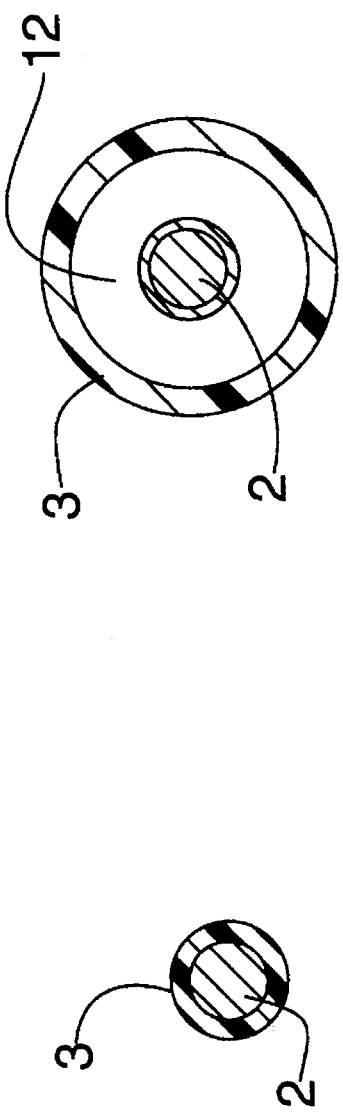

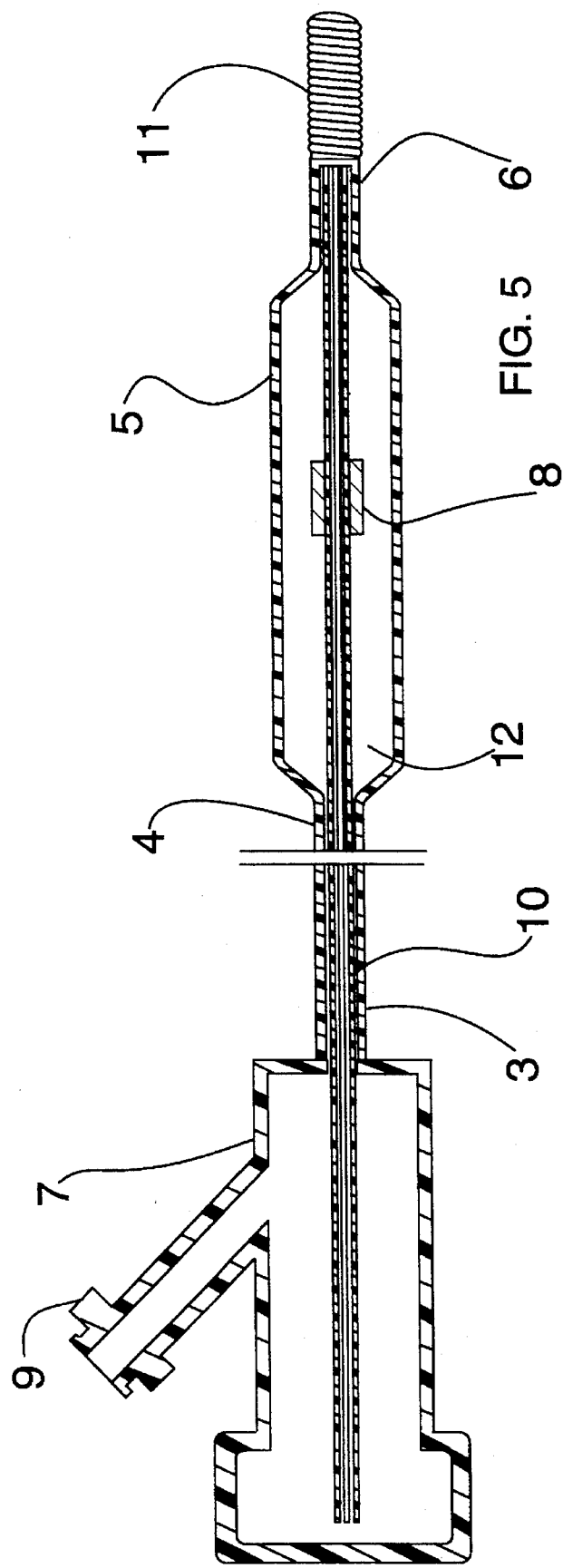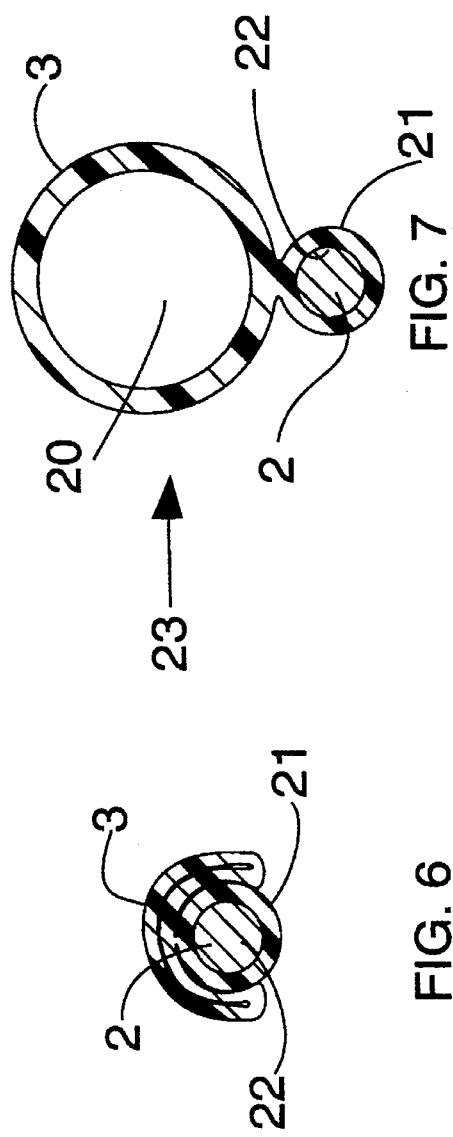

5,474,537

INFLATABLE SHAFT CATHETER

This application is a continuation of U.S. patent application Ser. No. 08/214,041, filed Mar. 16, 1994, now abandoned, which in turn is a continuation of U.S. patent application Ser. No. 07/859,219, filed Mar. 30, 1992, now abandoned.

FIELD OF THE INVENTION

This invention relates to an inflatable shaft catheter. More particularly, this invention relates to a balloon dilatation catheter comprising a balloon and an inflatable shaft concentric to a steering wire.

BACKGROUND OF THE INVENTION

The design of catheters and catheter systems for use in coronary angioplasty has previously been an exercise in compromise. To gain the benefit of some features, others had to be sacrificed. As a result, the design of percutaneous transluminal coronary angioplasty (PTCA) balloon catheters has moved toward the direction of single-feature niche products. For example, in very tight lesions where profile is the priority feature, balloon-on-wire catheters, which have lower profiles, are commonly used. To gain the low profile feature, steerability has been compromised and the ability to exchange catheters has been sacrificed. Monorail and over-the-wire PCTA systems provide exchangeability, but these systems are larger than the balloon-on-wire catheters. Attempts to make these systems smaller have been at the expense of steerability, pushability, trackability, and balloon deflation time. The challenge of incorporating all the features desired by the interventional cardiologist within the boundary that the device be as small as possible has been described as "trying to put ten pounds of stuff in a five pound bag." A means to accomplish this objective would be to have a catheter device in which the shaft diameter could be varied during the procedure.

Catheters having variable diameters are known in the literature. Fuqua, U.S. Pat. No. 4,601,713 discloses a variable diameter catheter where the catheter is folded in a longitudinal manner to reduce its diameter. The folded catheter is held within a separate retaining means to maintain its folded state. Thus, a separate retaining means is required.

According to Saab, U.S. Pat. No. 4,800,349, an over-the-wire balloon dilatation catheter has a collapsible sleeve and balloon at its distal end. The flexible, non-collapsible inner shaft has a smaller diameter at its distal end, and its larger proximal end contains an inner lumen and a balloon inflation lumen. The sleeve is disposed concentrically around the smaller distal portion of the shaft, and the annular space between said distal portion and the sleeve is in fluid communication with the balloon inflation lumen of the shaft.

Despite the advances represented by the above-described patents, there is still a need for a simplified, easy-to-manufacture variable diameter shaft balloon catheter, especially one having better, inherent steerability.

OBJECTS OF THE INVENTION

It is an object of the invention to provide an inflatable shaft catheter.

It is also an object of the invention to provide a balloon dilatation catheter comprising a dilatation balloon and an inflatable shaft concentric to a steering wire.

It is further object of the invention to provide a dilatation catheter system comprising:

a steering wire;

a dilatation balloon concentric to said steering wire; and a flexible, inflatable tubular member concentric to said steering wire and having proximal and distal ends, said distal end being in fluid connection with said dilatation balloon.

These and other objects of the invention will become more apparent from the discussion below.

BRIEF DESCRIPTION OF THE DRAWINGS

FIG. 2 is a cross-sectional view along A—A in FIG. 1;

FIG. 3 is a cross-sectional view of the distal end of the embodiment of FIG. 1, after inflation;

FIG. 4 is a cross-sectional view along B—B in FIG. 3;

FIG. 5 is a cross-sectional view of another embodiment of the invention;

FIGS. 6, 7 and 8 are cross-sectional views of a further embodiment of the invention; and FIG. 8 is a cross-sectional view of the distal end of an embodiment of the invention.

DETAILED DESCRIPTION OF THE INVENTION

Figure 1:
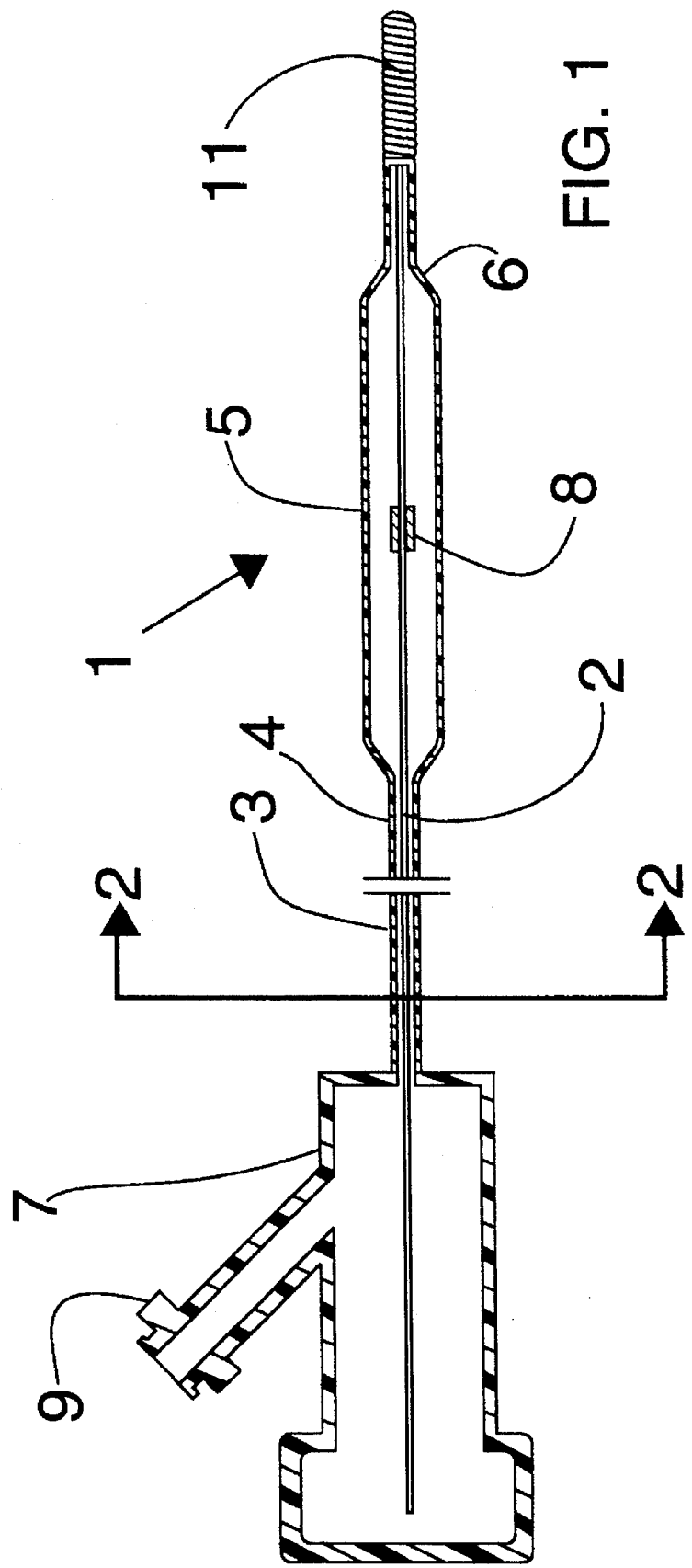
FIG. 1 is prospective cross-sectional view of an embodiment of the invention.

The invention herein is a balloon-on-wire, i.e., "fixed wire," PTCA catheter which preferably employs a floppy distal spring tip, a thin-walled high-strength balloon with a central radiopaque marker band, a steering wire with a solid internal core, and a thin membrane in place of a tubular catheter shaft. The internal core wire is larger than that of steerable guidewires and other balloon-on-wire PTCA catheters, which results in superior steerability and greater resistance to kinking. A uniquely designed construction of the core wire provides optimal pushability and trackability.

The balloon and shaft membrane are wrapped tightly around the core wire in a configuration that produces a balloon profile and catheter shaft diameter which are equivalent to that of the smallest devices on the market. Unlike other PTCA balloon catheters on the market, the membrane design of the invention precludes the need to "prep" the catheter (i.e., purge the air from the balloon and inflation lumen). This not only saves valuable time in the catheter lab, but also avoids the increase in balloon profile that results in most catheters during the "prep".

When the physician is ready to begin an angioplasty procedure, the inflatable shaft catheter of the invention is simply removed from its sterile package, introduced through a guiding catheter, and advanced to the target lesion. The very small diameter of the shaft allows excellent visualization, by means of contrast injection from the guiding catheter, thereby facilitating precise balloon placement. Once the balloon is in position across the lesion, contrast is injected into the inflatable shaft catheter in the same manner as with other balloon catheters. This causes the balloon and shaft to expand, i.e., inflate, to their respective inflated dimensions—the balloon to that of the artery adjacent to the lesion, and the shaft to a diameter smaller than that of the artery.

With the catheter of the invention there is a large ratio of the inflated shaft diameter to the internal core wire diameter, which provides a very large area within the catheter to inflate and deflate the balloon. This translates to a very rapid balloon inflation/deflation time feature. Moreover, unlike other balloon-on-wire catheters, the inflatable shaft catheter of the invention has no tubular shaft which can kink and result in impaired balloon inflation and deflation.

The unique and novel design of this invention provides the interventional cardiologist with all the desired features for a PTCA procedure—small balloon profile and shaft diameter, excellent steerability, trackability, and pushability, rapid inflation/deflation times, no prepping, ease of use—without compromise, in a single catheter. Moreover, with the exchange system described in co-pending, concurrently filed U.S. patent application Ser. No. 07/859,220, filed Mar. 30, 1992 (Case No. 3416-5), the inflatable shaft catheter of the invention can be safely and rapidly exchanged.

The inflatable shaft catheter of the invention can comprise a steering wire, a dilatation balloon, and an inflatable shaft in fluid connection with the balloon. Both the balloon and the inflatable shaft are concentric to the steering wire, and in a preferred embodiment, the inflatable shaft is in fluid connection with a control or inflation means.

The invention herein can perhaps be better appreciated by making reference to the drawings. As shown in FIG. 1, the inflatable shaft catheter 1 comprises a steering wire 2 and an inflatable shaft 3. The distal end 4 of the inflatable shaft 3 is adjacent to dilatation balloon 5. The distal portion 6 of balloon 5 is sealingly attached to steering wire 2, preferably by heat-sealing, heat-shrinking, or adhesive. As depicted in FIG. 2, uninflated or deflated inflatable shaft 3 collapses around steering wire 2.

Inflatable shaft 3 and balloon 5 are integral, that is, they form one piece. They can be formed from one continuous polymeric member or they can comprise two separate elements that are sealingly joined together, for example, by heat or adhesive.

The embodiment of FIG. 1 in inflated condition is shown in FIGS. 3 and 4. Inflatable shaft 3 is inflated first through a suitable port 9 in control means 7, and then balloon 5 is inflated.

Another embodiment of the invention is shown in FIG. 5, where an additional, inner tubular member 10 is concentric to steering wire 2. Inner tubular member 10, which extends from in or adjacent to control means 7 to about the proximal end of floppy wire 11, provides support and lubricity so that steering wire 2 can be rotated independently of inflatable shaft 3. Optimally steering wire 2 can be removed from inner tubular member 10. The distal end 6 of balloon 5 will be sealingly attached to the distal end of inner tubular member 10, preferably by heat-shrinking, heat-sealing, or adhesive.

Figure 8:
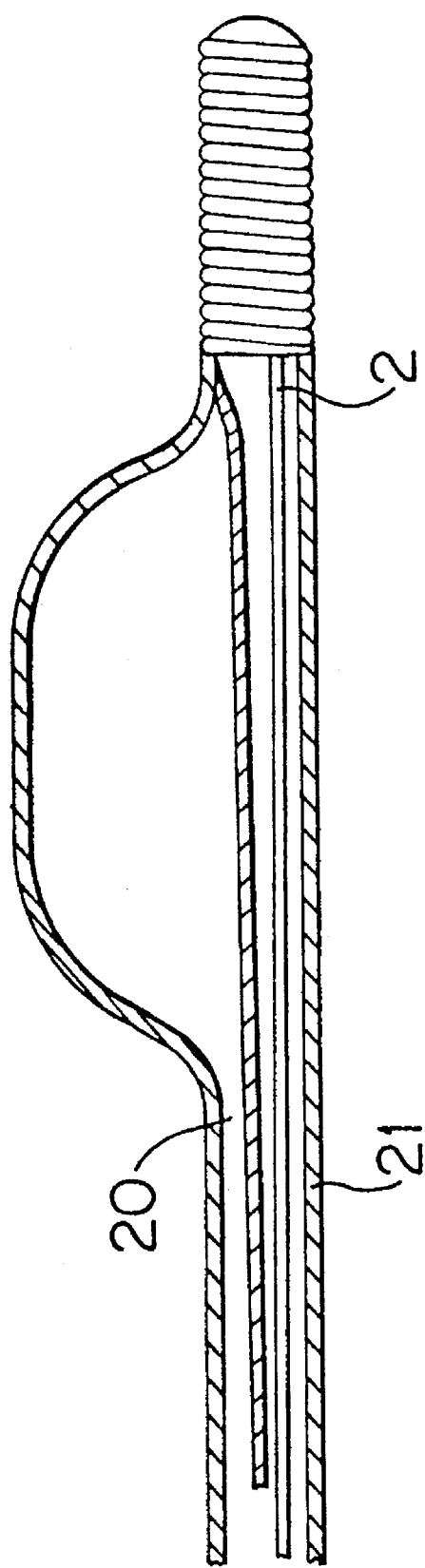

In the embodiment of the invention shown in FIGS. 6, 7 and 8 inflatable shaft 3 having lumen 20 is adjacent a second shaft 21 containing steering wire 2 in wire lumen 22. When lumen 20 is not inflated, inflatable shaft 3 collapses around second shaft 21, reducing the overall cross-sectional profile of catheter 23.

At the distal end of catheter 23 (not shown), the second shaft 21 may continue through a balloon, where the steering wire 2 enters the proximal portion of the balloon and exits the distal portion, into a continuation of second shaft 21 and lumen 20. In the alternative, second shaft 21 and lumen 20 could continue to the distal end of catheter 23, without a break or interruption.

Inflatable shaft 3 is comprised of a very thin, nondistending, high strength, polymeric material that is folded in a very small diameter cross-sectional configuration. Folding the inflatable shaft material into a small diameter allows adequate flow of blood and/or contrast material, e.g., to effect arterial fluoroscopic visualization, during advancement of the catheter to the target site, i.e., stenosis. The thickness of the material is from about 0.0001 to 0.0030 in., preferably from about 0.0002 to 0.0020 in. Suitable polymeric materials include polyurerethanes, polyesters, such as polyethyleneterephthalate (PET), polyethyleneterephthalate glycol (PETG), and copolymers thereof, polyolefins, such as polyethylene and copolymers thereof, polyvinylchloride, and the like.

Once the dilatation balloon is in desired position, pressurization of the inflatable shaft 3 causes the shaft to expand to its intended inflated diameter, e.g., from about 2 to 10 French (0.026 to 0.13 in.), preferably from about 3 to 5 French (0.039 to 0.065 in.). This will then increase the intraluminal space 12 within inflatable shaft 3 that is a conduit for the fluid to inflate balloon 5. This relatively large cross-sectional area 12 will permit rapid inflation and deflation of the dilatation balloon 5.

As is clear from the above, the shaft diameter of inflatable shaft 3 becomes larger as inflatable shaft 3 is inflated. Conversely, when balloon 5 and inflatable shaft 3 are deflated, the profile of inflatable shaft 3 decreases.

Balloon 5 will be a conventional size and constructed from polymeric materials typically used for this purpose. Typical such materials include polyesters, such as PET, PETG, and copolymers thereof, polyolefins, such as polyethylene and copolymers thereof, polyvinylchloride, and the like.

Steering wire 2 can be constructed to correspond to any conventional steering wire or guidewire, and the particular construction is not critical here. However, it is preferred that steering wire 2 have a larger diameter than typical core wires used in balloon-on-wire catheters or PTCA or PTA guidewires, for example, from about 0.014 to 0.04 in., more preferably from about 0.016 to 0.035 in.

It is within the scope of the invention that steering wire 2 may have a lubricous coating, e.g., PTFE, hydrogel, or a polysiloxane, or that it have one of several known configurations. Such configurations include, but are not limited to, coil spring, solid round wire, hypotube, flat, rectangular, or other geometrical cross-section, including , multifilar covered, braided wire, or the like. A hollow guidewire, e.g., a hypotube, could have one or more openings suitable for venting the dilatation balloon.

There are known steering wire or guidewire constructions that would be useful here. See, for example, U.S. Pat. Nos. 4,757,827, 4,815,478, 4,813,434, 4,619,274, 4,554,929, 4,545,390, 4,538,622, 3,906,938, 3,973,556, and 4,719,924, all which are incorporated herein by reference.

Inner tubular member 10 can be comprised of suitable flexible polymeric material such as is disclosed above for balloon 5 or shaft 3 or a spring optionally coated with a thin polymeric film. Also, inner tubular member 10 can have lubricous coating, e.g., PTFE, a hydrogel, or a polysiloxane, and it could optionally have openings in its distal end to permit venting of balloon 5. It is within the scope of the invention that the catheter system having inner tubular member 10 could be constructed to permit rotation and/or withdrawal of steering wire 2.

Furthermore, steering wire 2 or tubular member 10 may optionally, and preferably, have one or more radiopaque markers 8 to indicate the location of balloon 5 on a fluoroscope. Typical radiopaque materials include gold, platinum, tungsten, tantalum, and alloys thereof, and the like, which are affixed as bands, for example, is known manner.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A dilatation catheter comprising: a steering wire;

a dilatation balloon longitudinally encompassing said steering wire; and a flexible catheter shaft eccentric to the steering wire and in fluid communication with the balloon, wherein the catheter shaft can be inflated to increase the diameter of the catheter shaft to a predetermined size and the diameter of the catheter shaft decreases when the catheter shaft is deflated.

2. The catheter of claim 1, wherein the balloon has a distal portion sealingly attached to the steering wire.

3. The catheter of claim 1, wherein the balloon and the collapsible shaft are continuous.

4. The catheter of claim 1, wherein the collapsible shaft and the balloon are each comprised of material selected from the group consisting of polyurethanes, polyesters, polyolefins, and polyvinylchloride.

5. The catheter of claim 1, wherein the steering wire has a floppy tip at its distal end.

6. The catheter of claim 5, wherein the floppy tip comprises radiopaque material.

7. The catheter of claim 1, wherein the steering wire has one or more radiopaque markers positioned thereon.

8. A dilatation catheter comprising:

a steering wire;

a dilatation balloon longitudinally encompassing said steering wire; and a flexible catheter shaft eccentric to the steering wire and having proximal and distal ends, the distal end of the catheter shaft being in fluid communication with the balloon, such that the catheter shaft is inflatable to increase the diameter of the catheter shaft to a predetermined size, and the diameter of the catheter shaft decreases when the catheter shaft is deflated.

9. The catheter of claim 8, wherein the balloon has a distal portion sealingly attached to the steering wire.

10. The catheter of claim 8, wherein the balloon and the collapsible shaft are continuous.

11. The catheter of claim 8, wherein the collapsible shaft and the balloon are each comprised of material selected from the group consisting of polyurethanes, polyesters, polyolefins, and, polyvinylchloride.

12. The catheter of claim 8, wherein the steering wire has a floppy tip at its distal end.

13. The catheter of claim 12, wherein the floppy tip comprises radiopaque material.

14. The catheter of claim 8, wherein the steering wire has one or more radiopaque markers positioned thereon.

15. A dilatation catheter comprising:

a first catheter shaft having a longitudinally extending first lumen containing a steering wire and having proximal and distal ends;

a dilatation balloon at the distal end of the catheter shaft;

a second flexible catheter shaft having a second lumen adjacent and parallel to said first lumen and in fluid communication with the inner surface of said balloon, such that the catheter shaft is inflatable to increase the diameter of the catheter shaft to a predetermined size, and the diameter of the catheter shaft decreases when the catheter shaft is deflated.

\* \* \* \* \*